US011241592B2

(12) United States Patent
Lee et al.

(10) Patent No.: US 11,241,592 B2
(45) Date of Patent: Feb. 8, 2022

(54) METHOD FOR STIMULATING, AND APPARATUSES PERFORMING THE SAME

(71) Applicant: KOREA ADVANCED INSTITUTE OF SCIENCE AND TECHNOLOGY, Daejeon (KR)

(72) Inventors: Hyunjoo Lee, Daejeon (KR); HyungGuk Kim, Daejeon (KR); Seongyeon Kim, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 696 days.

(21) Appl. No.: 16/021,805

(22) Filed: Jun. 28, 2018

(65) Prior Publication Data

US 2019/0000426 A1    Jan. 3, 2019

(30) Foreign Application Priority Data

Jun. 30, 2017  (KR) .................. 10-2017-0083748

(51) Int. Cl.
*A61B 8/00*   (2006.01)
*A61N 1/04*   (2006.01)
(Continued)

(52) U.S. Cl.
CPC ............. *A61N 7/00* (2013.01); *A61N 1/0529* (2013.01); *A61N 1/0408* (2013.01);
(Continued)

(58) Field of Classification Search
CPC .......... A61N 8/54; A61N 17/225; A61N 7/00; A61N 1/0529; A61N 2007/0026;
(Continued)

(56) References Cited

U.S. PATENT DOCUMENTS 3,735,756 A * 5/1973 Richards ............ A61H 23/0245
                                                       601/2
4,646,756 A * 3/1987 Watmough ............... A61N 7/02
                                                       607/154
(Continued)

FOREIGN PATENT DOCUMENTS

| JP | 2011518629 A | 6/2011 |
| WO | 2015137749 A1 | 9/2015 |
| WO | 2015178680 A1 | 11/2015 |

*Primary Examiner* — Mark W. Bockelman
(74) *Attorney, Agent, or Firm* — Kacvinsky Daisak Bluni, PLLC

(57) ABSTRACT

Disclosed is a method and apparatus for more locally stimulating a desired stimulation region in a predetermined part of an object, the apparatus including a first ultrasonic wave generator configured to output a first ultrasonic beam to a predetermined part of an object, a second ultrasonic wave generator configured to output a second ultrasonic beam to the predetermined part of the object, and a controller configured to control the first ultrasonic wave generator and the second ultrasonic wave generator such that central axes of the first ultrasonic wave generator and the second ultrasonic wave generator are disposed on the same plane, and a crossing angle between the first ultrasonic beam and the second ultrasonic beam is a predetermined angle.

12 Claims, 13 Drawing Sheets

(51) Int. Cl.
*A61N 7/00* (2006.01)
*A61N 1/05* (2006.01)

(52) U.S. Cl.
CPC .... *A61N 1/0476* (2013.01); *A61N 2007/0021* (2013.01); *A61N 2007/0026* (2013.01); *A61N 2007/0078* (2013.01)

(58) Field of Classification Search
CPC .... A61N 2007/0078; A61N 2007/0021; A61N 1/0476; A61N 1/0408; A61N 1/36025; A61N 2007/0091; A61N 2007/0056
See application file for complete search history.

(56) References Cited

U.S. PATENT DOCUMENTS

| | | | |
|---|---|---|---|
| 5,725,482 A * | 3/1998 | Bishop | A61B 17/225 601/2 |
| 2012/0109020 A1 | 5/2012 | Wagner et al. | |
| 2015/0151142 A1 | 6/2015 | Tyler et al. | |

* cited by examiner

Single ultrasonic wave generator

Two ultrasonic wave generators (90° arrangement)

Graph for each ultrasonic parameter

Graph for each ultrasonic parameter

Graph for each ultrasonic parameter

Graph for each ultrasonic parameter

Phase difference 0° between
two ultrasonic wave generators
(90° arrangement)

Phase difference 180° between
two ultrasonic wave generators
(90° arrangement)

Phase difference 0° between
two ultrasonic wave generators
(45° arrangement)

Phase difference 180° between
two ultrasonic wave generators
(45° arrangement)

Photo of experiment for determining
effect of simultaneously applying
electrical stimulation (clips) and
ultrasonic stimulation
(single transducer)

Photo of experiment for determining
effect of simultaneously applying
electrical stimulation (clips) and
ultrasonic stimulation
(single transducer)

METHOD FOR STIMULATING, AND APPARATUSES PERFORMING THE SAME

CROSS-REFERENCE TO RELATED APPLICATION(S)

This application claims the priority benefit of Korean Patent Application No. 10-2017-0083748 filed on Jun. 30, 2017, in the Korean Intellectual Property Office, the disclosure of which is incorporated herein by reference for all purposes.

BACKGROUND

1. Field

One or more example embodiments relate to a method and apparatus for more locally stimulating a desired stimulation region in a predetermined part of an object.

2. Description of Related Art

An ultrasonic brain stimulator using an existing technology stimulates a relatively wide region. Thus, a brain region requiring no stimulation may be exposed to physical energy.

In addition, for non-invasive brain stimulation, an ultrasonic wave needs to pass through a skull, and an intensity of the ultrasonic wave is attenuated greatly when the ultrasonic wave passes through the skull. Thus, it is difficult to deliver a sufficient intensity of energy using a single ultrasonic device.

SUMMARY

An aspect provides technology that may maximize the stimulation efficiency and the stability by stimulating a desired region, for example, brain cells of the desired region, with minimal energy.

Another aspect also provides technology that may localize a stimulation region, increase the stimulation energy efficiency, and increase the stability by minimizing energy to be delivered to an inevitably exposed region.

According to an aspect, there is provided a stimulating apparatus including a first ultrasonic wave generator configured to output a first ultrasonic beam to a predetermined part of an object, a second ultrasonic wave generator configured to output a second ultrasonic beam to the predetermined part of the object, and a controller configured to control the first ultrasonic wave generator and the second ultrasonic wave generator such that central axes of the first ultrasonic wave generator and the second ultrasonic wave generator may be disposed on the same plane, and a crossing angle between the first ultrasonic beam and the second ultrasonic beam may be a predetermined angle.

The controller may be configured to control an arrangement position of at least one of the first ultrasonic wave generator and the second ultrasonic wave generator such that focus points of the first ultrasonic wave generator and the second ultrasonic wave generator may match.

The controller may be configured to control an output intensity of at least one of the first ultrasonic wave generator and the second ultrasonic wave generator such that intensities of the first ultrasonic beam and the second ultrasonic beam may be equalized at the focus points.

The stimulating apparatus may further include a power device configured to adjust an arrangement position of at least one of the first ultrasonic wave generator and the second ultrasonic wave generator.

The stimulating apparatus may further include a variable resistor configured to adjust a voltage to be applied to at least one of the first ultrasonic wave generator and the second ultrasonic wave generator.

The stimulating apparatus may further include a radio frequency (RF) amplifier configured to adjust a gain of the voltage to be applied to at least one of the first ultrasonic wave generator and the second ultrasonic wave generator.

The power device may be implemented as a three-dimensional (3D) axis motor.

The stimulating apparatus may further include an electro-stimulator configured to output an electrical stimulation to a crossing point between the first ultrasonic beam and the second ultrasonic beam in the predetermined part.

The electro-stimulator may include a plurality of electrodes positioned relative to the crossing point such that an electric field may be formed to pass through the crossing point, and an electric field generator configured to generate the electric field.

According to another aspect, there is also provided a stimulating method including outputting, by a first ultrasonic wave generator, a first ultrasonic beam to a predetermined part of an object, outputting, by a second ultrasonic wave generator, a second ultrasonic beam to the predetermined part of the object, and controlling the first ultrasonic wave generator and the second ultrasonic wave generator such that central axes of the first ultrasonic wave generator and the second ultrasonic wave generator may be disposed on the same plane, and a crossing angle between the first ultrasonic beam and the second ultrasonic beam may be a predetermined angle.

The controlling may include adjusting an arrangement position of at least one of the first ultrasonic wave generator and the second ultrasonic wave generator such that focus points of the first ultrasonic wave generator and the second ultrasonic wave generator may match.

The controlling may further include adjusting an output intensity of at least one of the first ultrasonic wave generator and the second ultrasonic wave generator such that intensities of the first ultrasonic beam and the second ultrasonic beam may be equalized at the focus points.

The adjusting of the output intensity may include adjusting a voltage to be applied to at least one of the first ultrasonic wave generator and the second ultrasonic wave generator.

The adjusting of the output intensity may further include adjusting a gain of the voltage to be applied to at least one of the first ultrasonic wave generator and the second ultrasonic wave generator.

The stimulating method may further include outputting an electrical stimulation to a crossing point between the first ultrasonic beam and the second ultrasonic beam in the predetermined part.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which.

DETAILED DESCRIPTION

Figure 1:
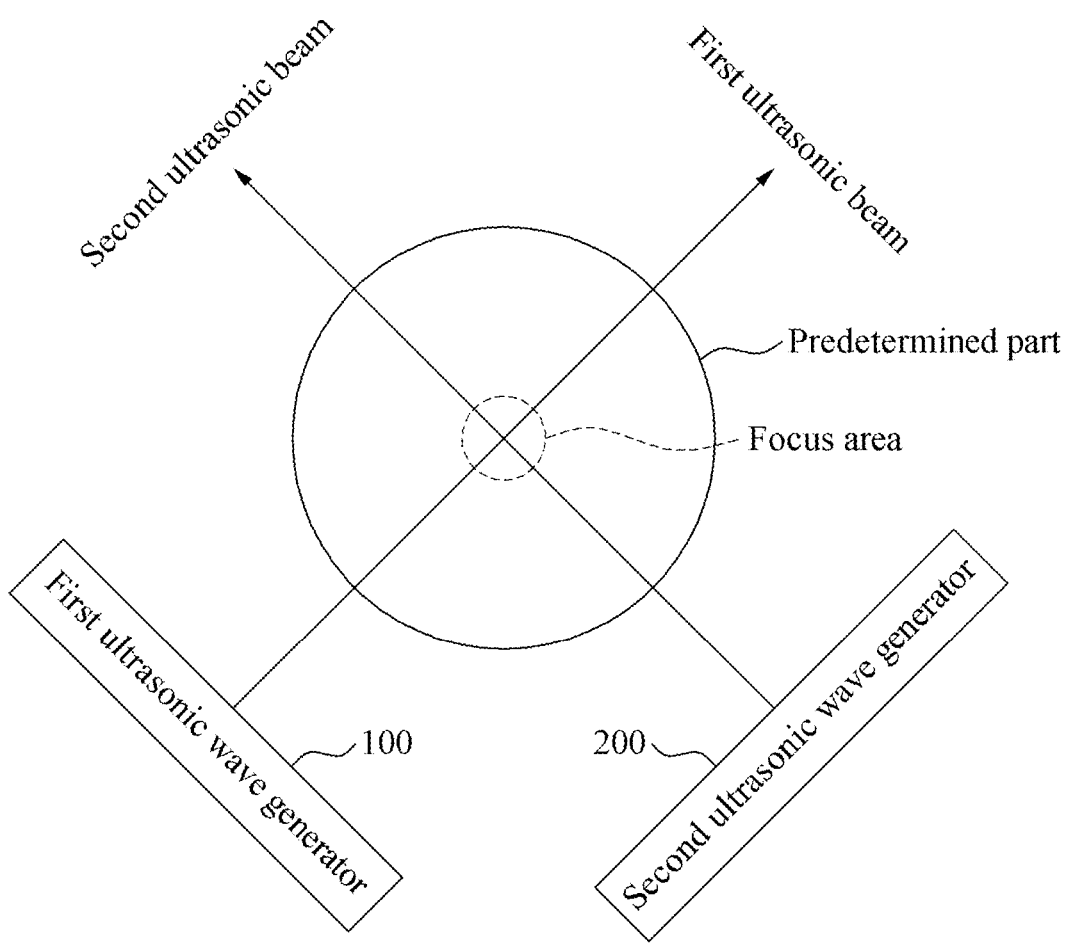
FIG. 1 is a diagram illustrating an operation of stimulating a predetermined part of an object according to an example embodiment.
Figure 2A:
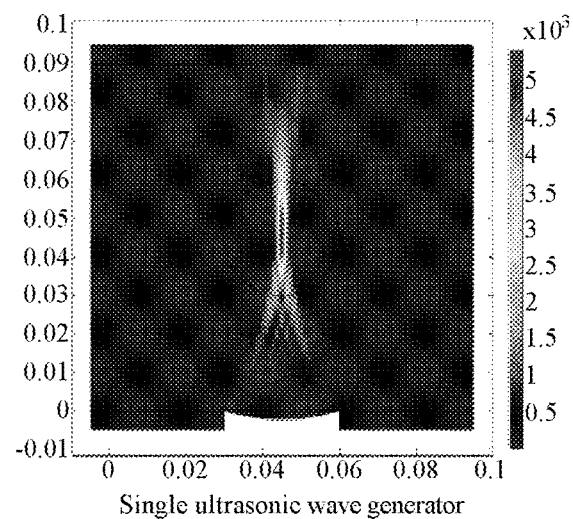
FIGS. 2A through 2D illustrate shapes of ultrasonic beams generated according to arrangements of ultrasonic wave generators.
Figure 2B:
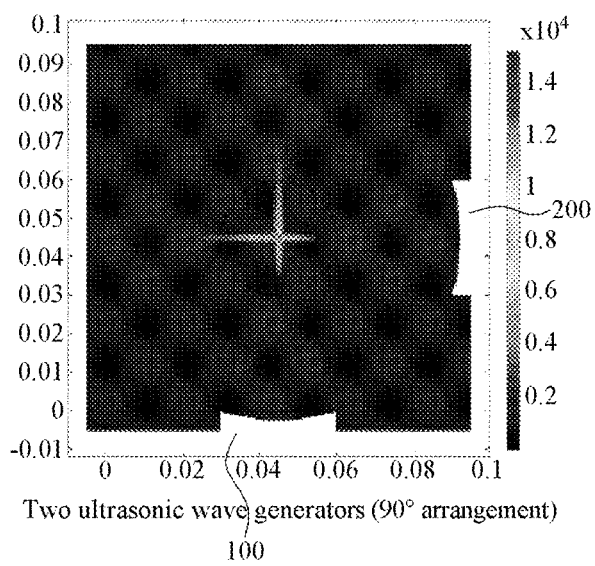
Figure 2C:
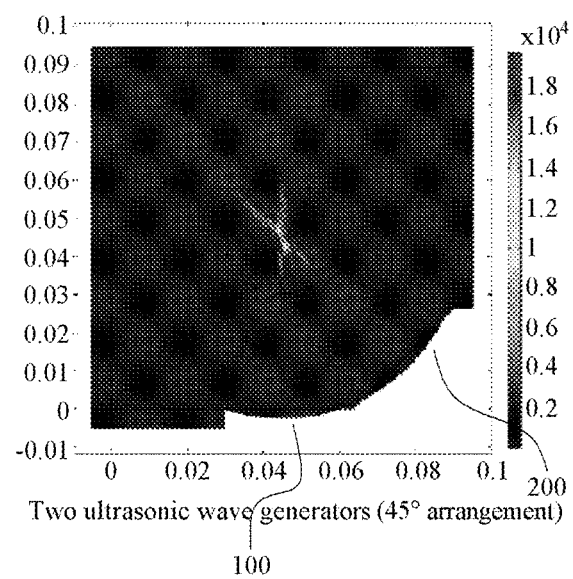
Figure 2D:
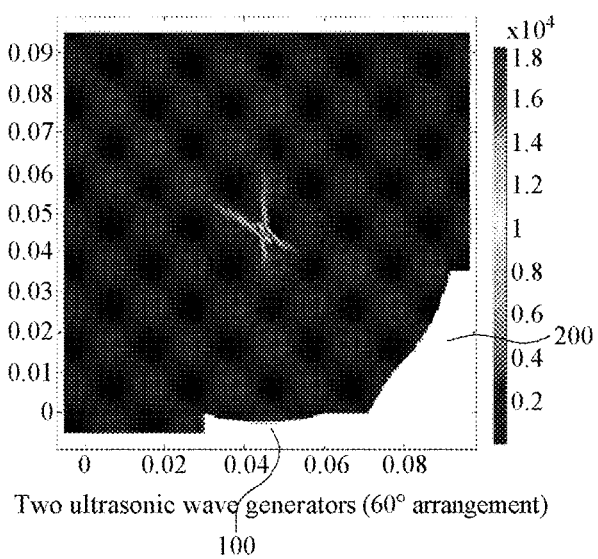
Figure 3A:
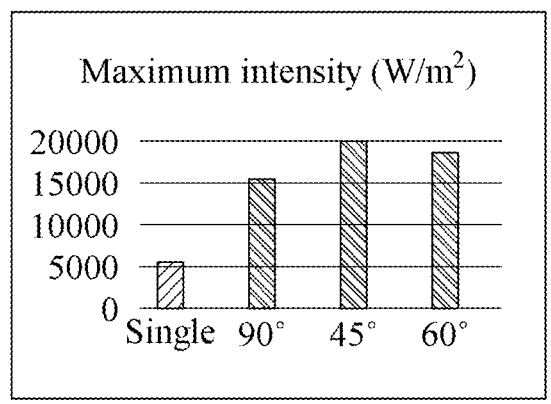
FIGS. 3A through 3D are graphs illustrating parameters of ultrasonic waves generated according to arrangements of ultrasonic wave generators.
Figure 3B:
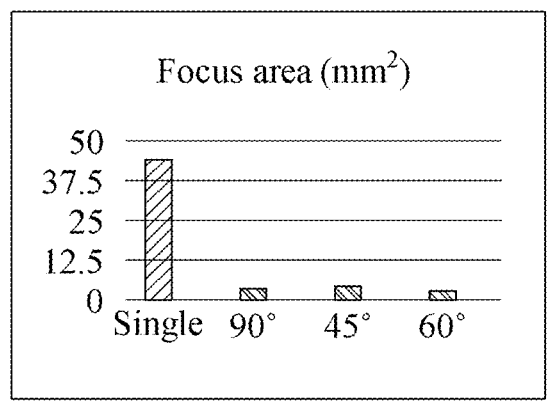
Figure 3C:
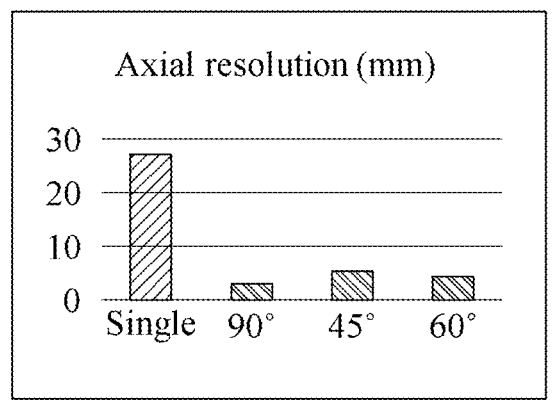
Figure 3D:
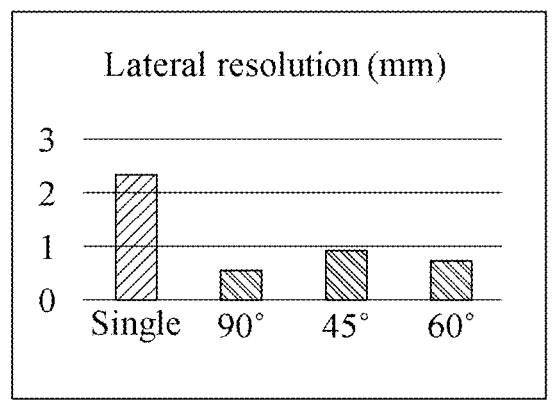
Figure 4A:
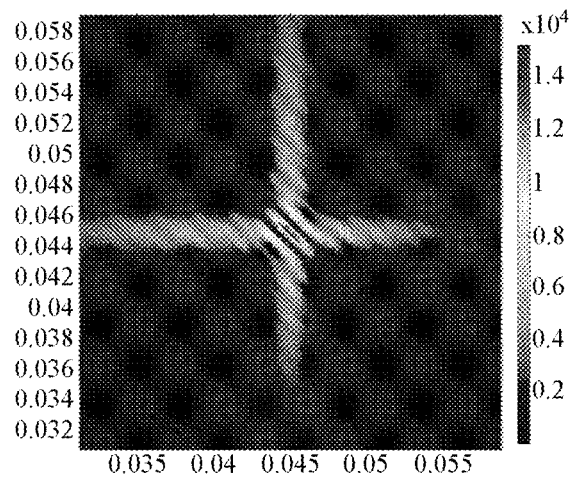
FIGS. 4A through 4D illustrate shapes of ultrasonic beams generated according to arrangements of ultrasonic wave generators.
Figure 4B:
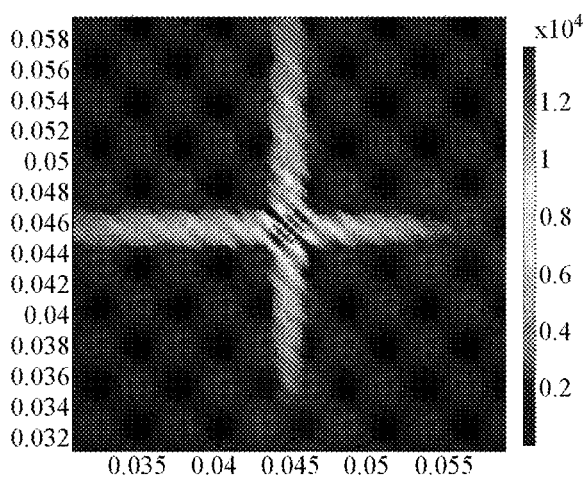
Figure 4C:
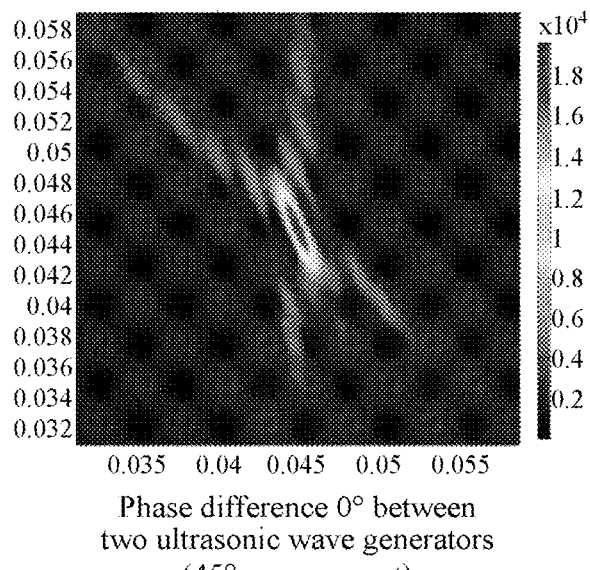
Figure 4D:
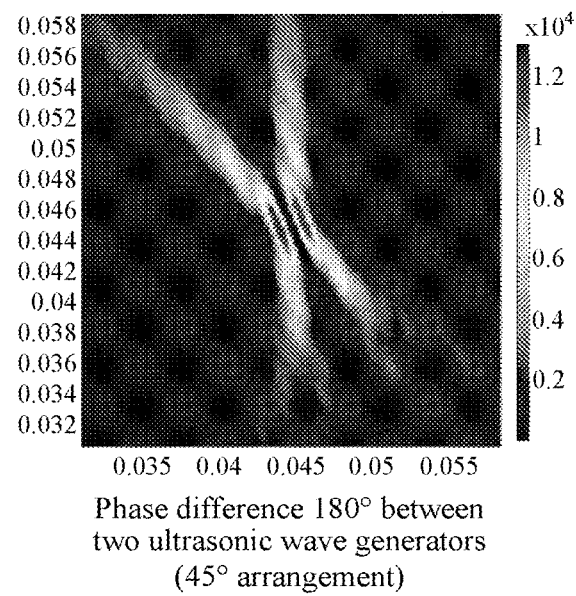

The following structural or functional descriptions are exemplary to merely describe the example embodiments, and the scope of the example embodiments is not limited to the descriptions provided herein.

Various alterations and modifications may be made to the examples. Here, the examples are not construed as limited to the disclosure and should be understood to include all changes, equivalents, and replacements within the idea and the technical scope of the disclosure.

Terms, such as first, second, and the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

It should be noted that if it is described that one component is "connected", "coupled", or "joined" to another component, a third component may be "connected", "coupled", and "joined" between the first and second components, although the first component may be directly connected, coupled, or joined to the second component. On the contrary, it should be noted that if it is described that one component is "directly connected", "directly coupled", or "directly joined" to another component, a third component may be absent. Expressions describing a relationship between components, for example, "between", directly between", or "directly neighboring", etc., should be interpreted to be alike.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which examples belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

Hereinafter, the example embodiments will be described in detail with reference to the accompanying drawings. However, the scope of the present application is not limited to the example embodiments. In the drawings, like reference numerals are used for like elements.

FIG. 1 is a diagram illustrating an operation of stimulating a predetermined part of an object according to an example embodiment.

Referring to FIG. 1, a first ultrasonic wave generator 100 may output a first ultrasonic beam to a predetermined part of an object. A second ultrasonic wave generator 200 may output a second ultrasonic beam to the predetermined part of the object. For example, the object may be a living thing, and the predetermined part of the object may be a brain.

In a case of outputting ultrasonic beams to the predetermined part of the object using the plurality of ultrasonic wave generators 100 and 200, a region stimulated by the ultrasonic beams in the predetermined part may be localized.

To localize the region stimulated by the ultrasonic beams in the predetermined part using the plurality of ultrasonic wave generators 100 and 200, arrangements of the plurality of ultrasonic wave generators 100 and 200 may be used.

For example, the first ultrasonic wave generator 100 and the second ultrasonic wave generator 200 may be disposed such that central axes (axial axes) of the first ultrasonic wave generator 100 and the second ultrasonic wave generator 200 may be disposed (or positioned) on the same plane, and a crossing angle between the first ultrasonic beam and the second ultrasonic beam may be a predetermined angle.

In this example, the first ultrasonic wave generator 100 and the second ultrasonic wave generator 200 may be disposed such that focus points or focal spots of the first ultrasonic wave generator 100 and the second ultrasonic wave generator 200 may match.

Further, to localize the region stimulated by the ultrasonic beams in the predetermined part using the plurality of ultrasonic wave generators 100 and 200, the plurality of ultrasonic wave generators 100 and 200 may be controlled such that intensities of ultrasonic beams (or ultrasonic waves) to be generated at the focus points may be equalized.

When the first ultrasonic wave generator 100 and the second ultrasonic wave generator 200 are disposed and the ultrasonic beams at the focus points are controlled as described above, a focus area generated as the first ultrasonic beam and the second ultrasonic beam cross may be reduced. For example, the focus area may be an area corresponding to a half of a maximum intensity of an ultrasonic mean, that is, a full width half maximum (FWHM).

Thus, the focus area generated as the first ultrasonic beam and the second ultrasonic beam cross in the predetermined part of the object may be localized, a region corresponding to the focus area in the predetermined part may be localized and stimulated, and an inevitably exposed region in the predetermined part may be minimized such that an unnecessary stimulation may not be delivered thereto.

FIGS. 2A through 2D illustrate shapes of ultrasonic beams generated according to arrangements of ultrasonic wave generators, and FIGS. 3A through 3D are graphs illustrating parameters of ultrasonic waves generated according to arrangements of ultrasonic wave generators.

In FIGS. 2A through 2D, cases in which the first ultrasonic wave generator 100 and the second ultrasonic wave generator 200 are disposed such that central axes (axial axes) of the two are on a single plane and a crossing angle of the central axes (or ultrasonic beams) is 90 degrees, 45 degrees, and 60 degrees are illustrated.

As shown in FIGS. 2A through 2D, in a case in which the first ultrasonic wave generator 100 and the second ultrasonic wave generator 200 are disposed such that the central axes of the first ultrasonic wave generator 100 and the second ultrasonic wave generator 200 are disposed on the same plane and the crossing angle is a predetermined angle, it may be verified that a focus area generated as a first ultrasonic beam and a second ultrasonic beam cross is reduced greatly, when compared to a case of using a single ultrasonic wave generator.

In this example, parameters of ultrasonic beams (for example, ultrasonic beams in the focus area generated as the first ultrasonic beam and the second ultrasonic beam cross) generated in a case of using a single ultrasonic wave generator and cases of using arrangements of the plurality of ultrasonic wave generators 100 and 200 may be as shown in Table 1.

TABLE 1

|  | Single | 90° arrangement | 45° arrangement | 60° arrangement |
| --- | --- | --- | --- | --- |
| Max I [W/m$^2$] | 5454 | 15272 | 19770 | 18492 |
| Focus area [mm$^2$] | 44.2 | 2.9 | 4.1 | 2.5 |
| Axial resolution [mm] | 27.3 | 2.9 | 5.4 | 4.2 |
| Lateral resolution [mm] | 2.40 | 0.52 | 0.91 | 0.71 |

Further, the parameters of the ultrasonic beams of Table 1 may be arranged as shown in FIGS. 3A through 3D. As shown in Table 1 and FIGS. 3A through 3D, in the cases of using the arrangements of the plurality of ultrasonic wave generators 100 and 200, the focus area of the ultrasonic beams (for example, the ultrasonic beams in the focus area generated as the first ultrasonic beam and the second ultrasonic beam cross), an axial resolution, and a lateral resolution may be reduced greatly. In this example, intensities of the ultrasonic beams may increase in the focus area.

That is, in a case of using the arrangements of the plurality of ultrasonic wave generators 100 and 200, a region stimulated by ultrasonic beams in a predetermined part may be localized, and intensities of the ultrasonic beams in the stimulated region may increase. Thus, in a case in which the predetermined part is a brain, the ultrasonic beams may easily pass through a skull, and intensities of ultrasonic beams output from the plurality of ultrasonic wave generators 100 and 200 may be reduced.

Although FIGS. 2A through 2D illustrate only the cases in which the crossing angle of the central axes (or the ultrasonic beams) of the first ultrasonic wave generator 100 and the second ultrasonic wave generator 200 is 90 degrees, 45 degrees, and 60 degrees, example embodiments are not limited thereto. The crossing angle may be set to be greater than or less than a predetermined angle, for example, 90 degrees.

FIGS. 4A through 4D illustrate shapes of ultrasonic beams generated according to arrangements of ultrasonic wave generators.

In FIGS. 4A through 4D, cases in which the first ultrasonic wave generator 100 and the second ultrasonic wave generator 200 are disposed such that central axes (axial axes) of the two are on a single plane and a crossing angle of the central axes (or ultrasonic beams) is 90 degrees and 45 degrees, and there is a difference between a distance from a focus point to the first ultrasonic wave generator 100 and a distance from a focus point to the second ultrasonic wave generator 200 are illustrated.

Changes in the distance from the focus point to the first ultrasonic wave generator 100 and the distance from the focus point to the second ultrasonic wave generator 200 may cause phase changes in the ultrasonic beams output from the respective ultrasonic wave generators 100 and 200. In this example, it may be verified that a focus area generated as a first ultrasonic beam and a second ultrasonic beam cross is reduced, when compared to a case of using a single ultrasonic wave generator.

However, as shown in FIGS. 4A through 4D, when compared to a case in which there is no change in the distance from the focus point to the first ultrasonic wave generator 100 and the distance from the focus point to the second ultrasonic wave generator 200, in a case in which there are changes in the distance from the focus point to the first ultrasonic wave generator 100 and the distance from the focus point to the second ultrasonic wave generator 200, the localization of the focus area may be performed imperfectly and a stimulation shape corresponding to the focus area may be changed.

That is, in a case in which the first ultrasonic wave generator 100 and the second ultrasonic wave generator 200 are disposed such that the focus points of the first ultrasonic wave generator 100 and the second ultrasonic wave generator 200 may match, the stimulation shape corresponding to the focus area may be formed well such that the localization of the focus area may be performed more effectively, and the stimulation may be delivered well. Thus, the localized stimulation region may receive the stimulation more effectively.

In this example, by controlling the plurality of ultrasonic wave generators 100 and 200 such that intensities of ultrasonic beams (or ultrasonic waves) to be generated by the plurality of ultrasonic wave generators 100 and 200 at the focus points may be equalized, the localization of the focus area may be achieved more effectively, and the stimulation shape corresponding to the focus area may be formed well such that the stimulation may be delivered well.

Figure 5:
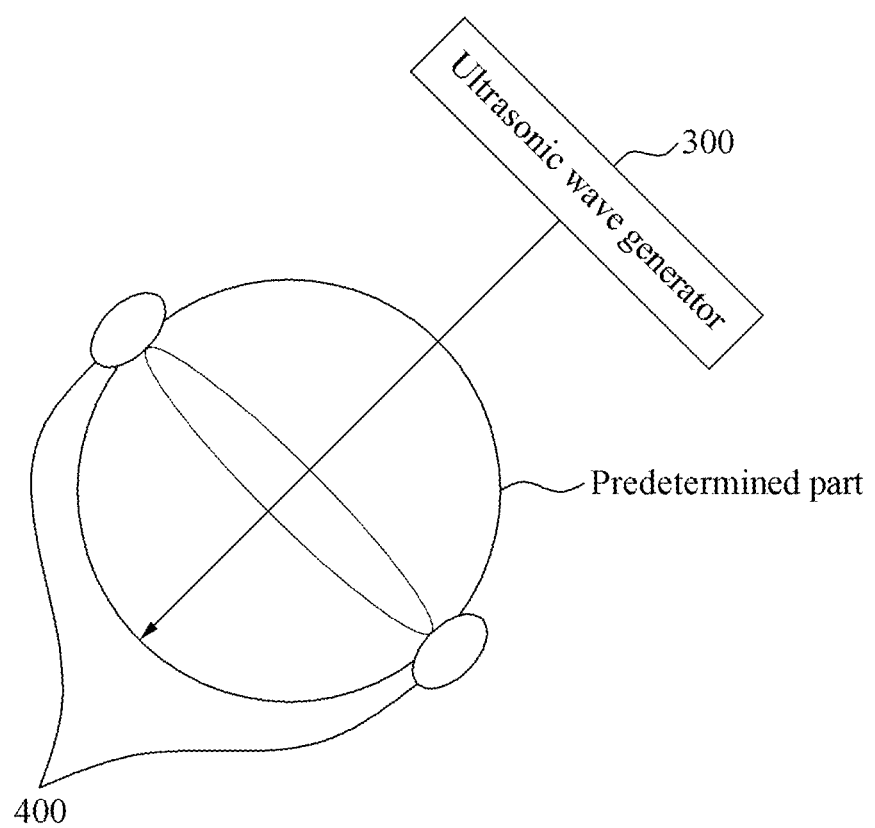
FIG. 5 illustrates an operation of stimulating a predetermined part of an object according to an example embodiment.
Figure 6A:
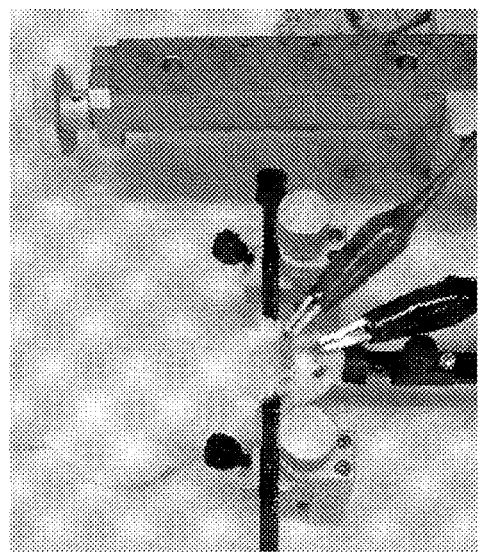
FIGS. 6A and 6B are photos of an experiment for determining an effect of the operation of stimulating a predetermined part described in FIG. 5.
Figure 6B:
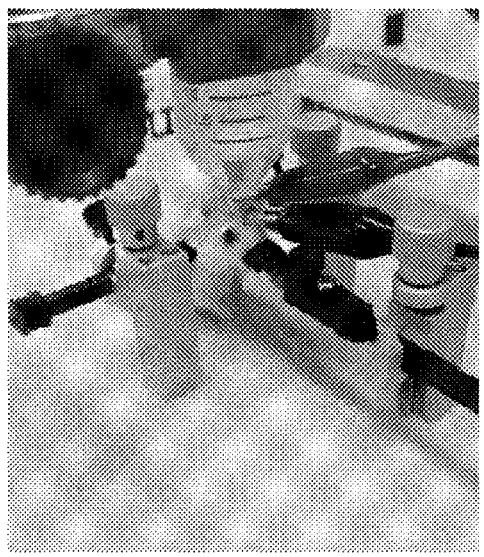
Figure 7:
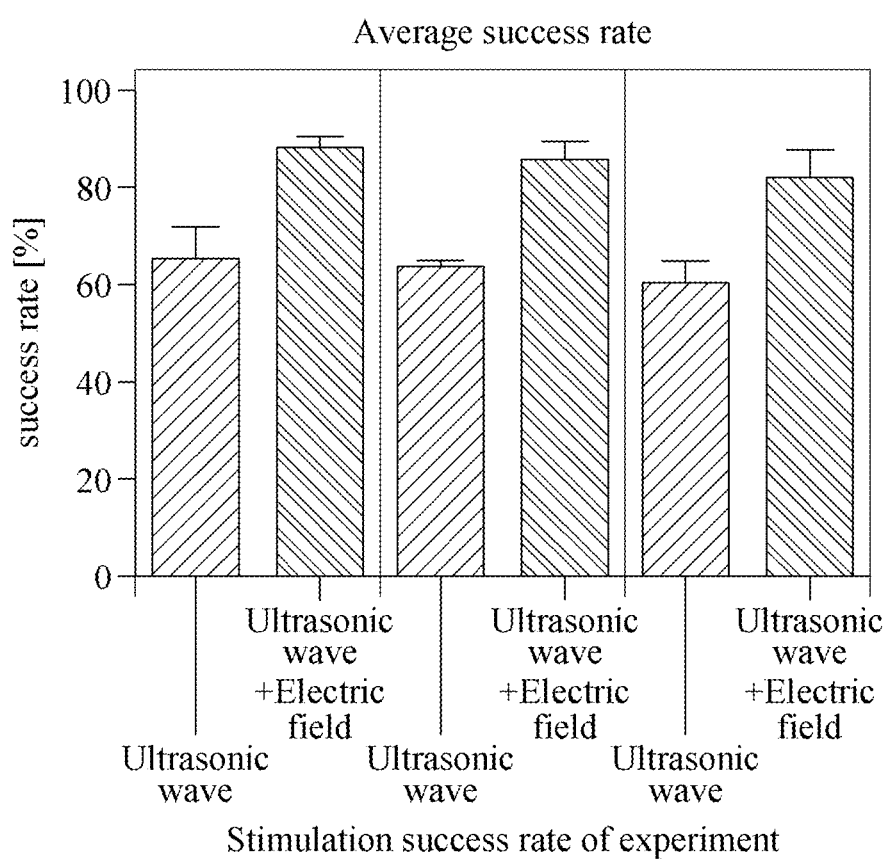
FIG. 7 illustrates stimulation success rates of the experiment of FIG. 6.

FIG. 5 illustrates an operation of stimulating a predetermined part of an object according to an example embodiment, FIGS. 6A and 6B are photos of an experiment for determining an effect of the operation of stimulating a predetermined part described in FIG. 5, and FIG. 7 illustrates stimulation success rates of the experiment of FIG. 6.

Referring to FIG. 5, an ultrasonic wave generator 300 may output an ultrasonic beam to a predetermined part of an object. An electro-stimulator 400 may output an electric field to the predetermined part of the object.

In a case of simultaneously applying an ultrasonic stimulation by the ultrasonic wave generator 300 and an electrical stimulation (or electric field stimulation) by the electro-stimulator 400 to the predetermined part, the stimulation efficiency at a crossing point of the two stimulations in the predetermined part may increase.

Thresholds for the ultrasonic stimulation by the ultrasonic wave generator 300 and the electrical stimulation by the electro-stimulator 400 may be lowered. That is, output intensities (or output energy) of the ultrasonic wave generator 300 and the electro-stimulator 400 may be lowered. Thus, a region inevitably exposed to the ultrasonic stimulation and/or the electrical stimulation, other than the crossing point of the two stimulations in the predetermined part, may be reduced, whereby the stability may be assured.

FIGS. 6 and 7 illustrate in vivo experiment results for a case of simultaneously applying two stimulations. In the case of applying an electrical stimulation and an ultrasonic stimulation at the same time through an in vivo experiment, it may be verified that the two stimulations create a synergy effect to increase a success rate of brain cell stimulation.

That is, if an ultrasonic stimulation and an electrical stimulation are applied simultaneously in a case of desiring to apply stimulations of the same efficiency to a stimulation region, the ultrasonic wave generator 300 may only have to output an ultrasonic beam (or ultrasonic wave) of a lower intensity to the stimulation region.

Since the stimulations of the same effect may be delivered to the stimulation region at a relatively low ultrasonic intensity, the stimulations may be delivered to the stimulation region effectively, and a stimulation area (for example, focus area) may be localized.

Figure 8:
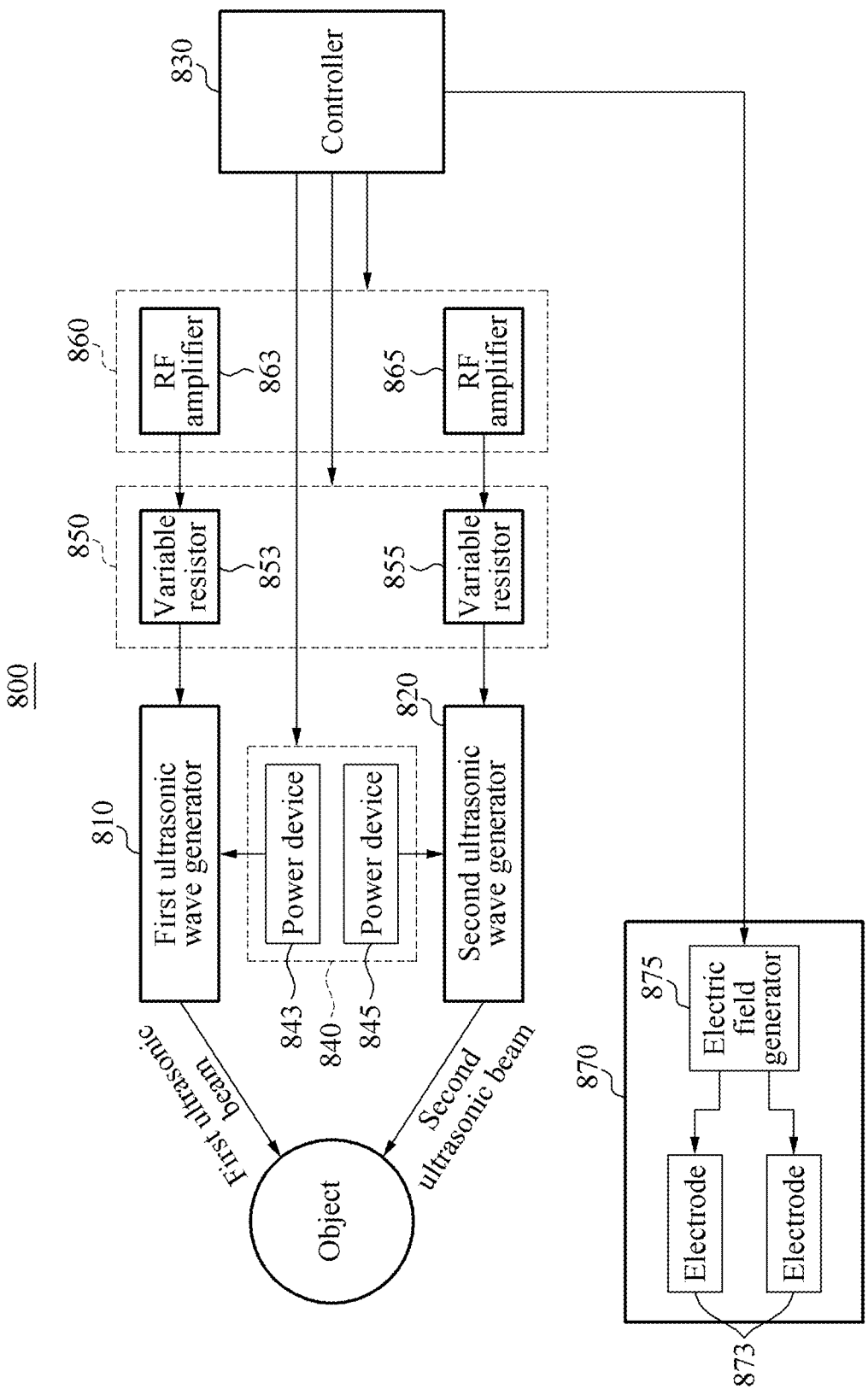
FIG. 8 is a block diagram illustrating an object stimulating apparatus according to an example embodiment.

FIG. 8 is a block diagram illustrating an object stimulating apparatus according to an example embodiment.

Referring to FIG. 8, an object stimulating apparatus 800 may stimulate a desired region (for example, brain cells or stimulation region) in a predetermined part (for example, brain) of an object, for example, a living thing. The object stimulating apparatus 800 may be a brain stimulator.

The object stimulating apparatus 800 may include a plurality of ultrasonic wave generators 810 and 820 and a controller 830. The object stimulating apparatus 800 may further include a power device 840, a variable resistor 850, and an radio frequency (RF) amplifier 860. The object stimulating apparatus 800 may further include an electro-stimulator 870.

The first ultrasonic wave generator 810 may output a first ultrasonic beam to the predetermined part of the object. The second ultrasonic wave generator 820 may output a second ultrasonic beam to the predetermined part of the object. Each of the ultrasonic wave generators 810 and 820 may be implemented as an ultrasonic transducer. For example, the ultrasonic transducer may be manufactured with a curved surface to focus an ultrasonic beam.

The controller 830 may control an overall operation of the object stimulating apparatus 800. For example, the controller 830 may control operations of the elements 810, 820, 840, 850, 860 and 870 of the object stimulating apparatus 800.

The controller 830 may control an arrangement position of at least one of the first ultrasonic wave generator 810 and the second ultrasonic wave generator 820.

The power device 840 may adjust the arrangement position of at least one of the first ultrasonic wave generator 810 and the second ultrasonic wave generator 820 based on a control of the controller 830. For example, the power device 840 may be implemented as a three-dimensional (3D) axis motor.

The power device 840 may include power devices 843 and 845 implemented with respect to the ultrasonic generators 810 and 820 to adjust arrangement positions of the ultrasonic generators 810 and 820, respectively.

When the controller 830 adjusts the arrangement position of at least one of the first ultrasonic wave generator 810 and the second ultrasonic wave generator 820 through the power device 840, central axes of the first ultrasonic wave generator 810 and the second ultrasonic wave generator 820 may be disposed on the same plane, and a crossing angle between the first ultrasonic beam and the second ultrasonic beam may be a predetermined angle. Further, focus points of the first ultrasonic wave generator 810 and the second ultrasonic wave generator 820 may match.

Further, the controller 830 may control an output intensity (or output strength) of at least one of the first ultrasonic wave generator 810 and the second ultrasonic wave generator 820.

Further, the controller 830 may control the output intensity of at least one of the first ultrasonic wave generator 810 and the second ultrasonic wave generator 820 such that intensities of the first ultrasonic beam and the second ultrasonic beam may be equalized at the focus points.

The variable resistor 850 may adjust a voltage to be applied to at least one of the first ultrasonic wave generator 810 and the second ultrasonic wave generator 820 based on a control of the controller 830.

The variable resistor 850 may include variable resistors 853 and 855 implemented with respect to the ultrasonic generators 810 and 820 to adjust voltages to be applied to the ultrasonic generators 810 and 820, respectively.

The RF amplifier 860 may adjust a gain of the voltage to be applied to at least one of the first ultrasonic wave generator 810 and the second ultrasonic wave generator 820 based on a control of the controller 830.

The RF amplifier 860 may include RF amplifiers 863 and 865 implemented with respect to the ultrasonic generators 810 and 820 to adjust gains of the voltages to be applied to the ultrasonic generators 810 and 820, respectively.

When the controller 830 adjusts the output intensity of at least one of the first ultrasonic wave generator 810 and the second ultrasonic wave generator 820 through the variable resistor 850 and/or the RF amplifier 860, the intensities of the first ultrasonic beam and the second ultrasonic beam may be equalized at the matching focus point of the first ultrasonic wave generator 810 and the second ultrasonic wave generator 820.

The object stimulating apparatus 800 may adjust the arrangement position of at least one of the first ultrasonic wave generator 810 and the second ultrasonic wave generator 820 and control the intensities of the first ultrasonic beam and the second ultrasonic beam at the focus points, thereby localizing a focus area generated as the first ultrasonic beam and second ultrasonic beam cross in the predetermined part of the object.

In this example, the object stimulating apparatus 800 may output an electrical stimulation to a crossing point between the first ultrasonic beam and the second ultrasonic beam in the predetermined part through the electro-stimulator 870, thereby increasing the stimulation efficiency at a stimulation region corresponding to the focus area.

The electro-stimulator 870 may include a plurality of electrodes 873 and an electric field generator 875. The plurality of electrodes 873 may be positioned relative to the crossing point such that an electric field may be formed to pass through the crossing point. The electric field generator 875 may generate the electric field, and output the electric field through the plurality of electrodes 873. The plurality of electrodes 873 may be positioned relative to the crossing point such that the first ultrasonic beam, the second ultrasonic beam and the electric field may be formed to cross at the crossing point.

Figure 9:
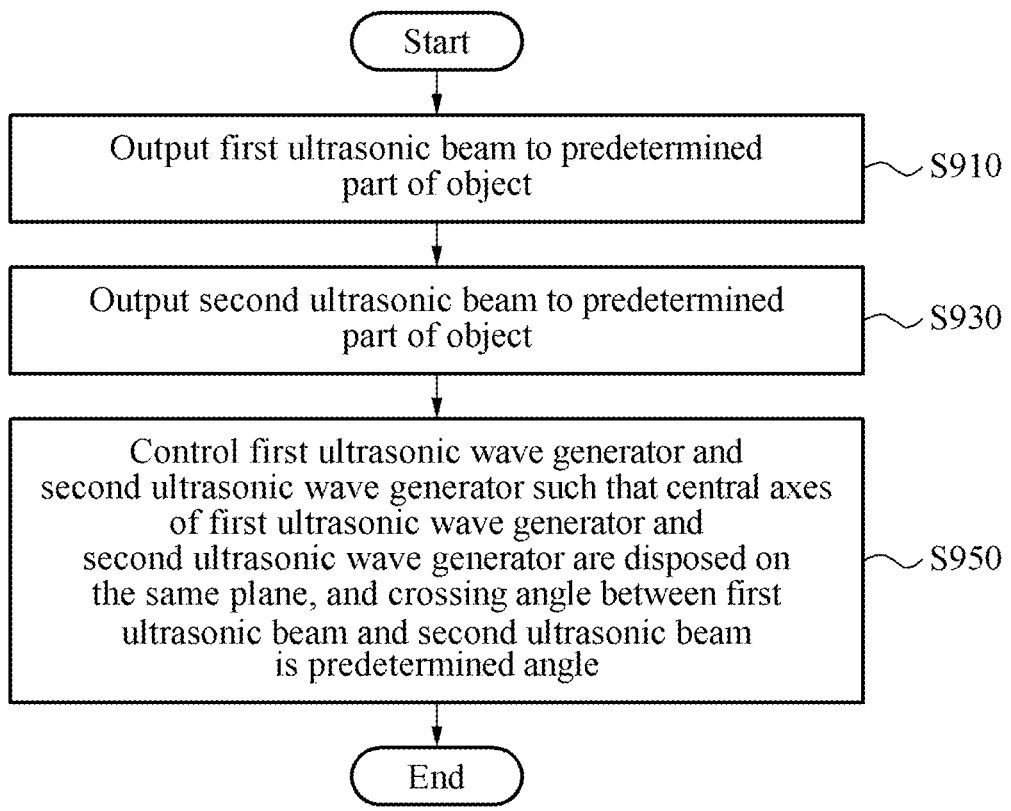
FIG. 9 is a flowchart illustrating an operating method of the object stimulating apparatus of FIG. 8.

FIG. 9 is a flowchart illustrating an operating method of the object stimulating apparatus of FIG. 8.

Referring to FIG. 9, in operation S910, the first ultrasonic wave generator 810 may output a first ultrasonic beam to a predetermined part of an object. In operation S930, the second ultrasonic wave generator 820 may output a second ultrasonic beam to the predetermined part of the object.

In operation S950, the controller 830 may control the first ultrasonic wave generator 810 and the second ultrasonic wave generator 820 such that central axes of the first ultrasonic wave generator 810 and the second ultrasonic wave generator 820 may be disposed on the same plane, and a crossing angle between the first ultrasonic beam and the second ultrasonic beam may be a predetermined angle.

The above example embodiments may more locally stimulate brain cells of an object, for example, a living thing, and more effectively deliver energy thereto than an existing technology.

The example embodiments may be helpful for various brain diseases such as Alzheimer's disease, Lou Gehrig's disease and depression, or metal illness, expected to have effects on exercise capacity, concentration and sleeping through brain stimulation, and contribute to development of various studies such as brain circuit investigations and experiments using brain stimulation.

Further, when implementing the above-mentioned possibilities, unnecessary stimulation of brain parts or tissues may be minimized, whereby side effects or unintended results may be reduced.

The example embodiments relate to an apparatus that may be applied to animal testing for research on various brain diseases or brain circuit investigations and brain disease treatments through physical therapy, and may be applicable to a wide range of fields associated with the brain.

The processing device described herein may be implemented using hardware components, software components, and/or a combination thereof. For example, the processing device and the component described herein may be implemented using one or more general-purpose or special purpose computers, such as, for example, a processor, a controller and an arithmetic logic unit (ALU), a digital signal processor, a microcomputer, a field programmable gate array (FPGA), a programmable logic unit (PLU), a microprocessor, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and/or multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A stimulating apparatus, comprising:
   a first ultrasonic wave generator configured to output a first ultrasonic beam to a predetermined part of an object;
   a second ultrasonic wave generator configured to output a second ultrasonic beam to the predetermined part of the object;
   a controller configured to control the first ultrasonic wave generator and the second ultrasonic wave generator such that central axes of the first ultrasonic wave generator and the second ultrasonic wave generator are disposed on the same plane, and a crossing angle between the first ultrasonic beam and the second ultrasonic beam is a predetermined angle, wherein the controller is configured to control an arrangement position of at least one of the first ultrasonic wave generator and the second ultrasonic wave generator at the predetermined angle such that focus points of the first ultrasonic wave generator and the second ultrasonic wave generator match to form a focus area, the focus area to comprise an area corresponding to at least half of a maximum intensity of an ultrasonic beam; and
   an electro-stimulator comprising: (i) a plurality of electrodes positioned relative to a crossing point between the first ultrasonic beam and the second ultrasonic beam in the predetermined part that forms the focus area and (ii) an electric field generator configured to generate an electric field via the plurality of electrodes such that the electric field is formed to pass through the crossing point at a stimulation region corresponding to the focus area.

2. The stimulating apparatus of claim 1, wherein the focus area to comprise an area corresponding to at least a full width half maximum (FWHM).

3. The stimulating apparatus of claim 2, wherein the controller is configured to control an output intensity of at least one of the first ultrasonic wave generator and the second ultrasonic wave generator such that intensities of the first ultrasonic beam and the second ultrasonic beam are equalized at the focus points.

4. The stimulating apparatus of claim 1, further comprising:
a power device configured to adjust an arrangement position of at least one of the first ultrasonic wave generator and the second ultrasonic wave generator.

5. The stimulating apparatus of claim 4, further comprising:
a variable resistor configured to adjust a voltage to be applied to at least one of the first ultrasonic wave generator and the second ultrasonic wave generator.

6. The stimulating apparatus of claim 5, further comprising:
a radio frequency (RF) amplifier configured to adjust a gain of the voltage to be applied to at least one of the first ultrasonic wave generator and the second ultrasonic wave generator.

7. The stimulating apparatus of claim 4, wherein the power device is implemented as a three-dimensional (3D) axis motor.

8. A stimulating method, comprising:
outputting, by a first ultrasonic wave generator, a first ultrasonic beam to a predetermined part of an object;
outputting, by a second ultrasonic wave generator, a second ultrasonic beam to the predetermined part of the object;
controlling, by a controller, the first ultrasonic wave generator and the second ultrasonic wave generator such that central axes of the first ultrasonic wave generator and the second ultrasonic wave generator are disposed on the same plane and that a crossing angle between the first ultrasonic beam and the second ultrasonic beam is a predetermined angle, wherein the controlling comprises adjusting an arrangement position of at least one of the first ultrasonic wave generator and the second ultrasonic wave generator at the predetermined angle such that focus points of the first ultrasonic wave generator and the second ultrasonic wave generator match to form a focus area, the focus area to comprise an area corresponding to at least half of a maximum intensity of an ultrasonic beam; and
generating, via an electro-stimulator, an electric field and forming the electric field to pass through a crossing point between the first ultrasonic beam and the second ultrasonic beam in the predetermined part.

9. The stimulating method of claim 8, wherein the focus area to comprise an area corresponding to at least a full width half maximum (FWHM).

10. The stimulating method of claim 8, wherein the controlling further comprises adjusting an output intensity of at least one of the first ultrasonic wave generator and the second ultrasonic wave generator such that intensities of the first ultrasonic beam and the second ultrasonic beam are equalized at the focus points.

11. The stimulating method of claim 10, wherein the adjusting of the output intensity comprises adjusting a voltage to be applied to at least one of the first ultrasonic wave generator and the second ultrasonic wave generator.

12. The stimulating method of claim 11, wherein the adjusting of the output intensity further comprises adjusting a gain of the voltage to be applied to at least one of the first ultrasonic wave generator and the second ultrasonic wave generator.

* * * * *